(12) United States Patent
Masumoto

(10) Patent No.: US 8,649,844 B2
(45) Date of Patent: Feb. 11, 2014

(54) MEDICAL IMAGE DIAGNOSIS ASSISTING APPARATUS, METHOD, AND PROGRAM

(75) Inventor: Jun Masumoto, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/279,494

(22) Filed: Oct. 24, 2011

(65) Prior Publication Data

US 2012/0101368 A1    Apr. 26, 2012

(30) Foreign Application Priority Data

Oct. 25, 2010    (JP) .................................. 2010-238439

(51) Int. Cl.
    *A61B 5/05*    (2006.01)
(52) U.S. Cl.
    USPC ........... 600/407; 600/410; 600/424; 600/425; 600/430; 600/431; 600/436; 600/437; 600/473; 600/476
(58) Field of Classification Search
    USPC ......... 600/407, 410, 424, 425, 430, 431, 436, 600/437, 473, 476
    See application file for complete search history.

(56) References Cited

U.S. PATENT DOCUMENTS

| | | | |
|---|---|---|---|
| 2007/0014452 A1 * | 1/2007 | Suresh et al. | ................. 382/128 |
| 2007/0236491 A1 | 10/2007 | Hundley et al. | |
| 2009/0096787 A1 | 4/2009 | Masumoto et al. | |
| 2010/0074487 A1 | 3/2010 | Miyamoto et al. | |
| 2010/0266176 A1 | 10/2010 | Masumoto et al. | |

FOREIGN PATENT DOCUMENTS

| | | |
|---|---|---|
| JP | 2007-307358 A | 11/2007 |
| JP | 2008-253753 A | 10/2008 |
| JP | 2008-259696 A | 10/2008 |

OTHER PUBLICATIONS

Takeshi Ishimoto, et al., "Studies of Three-dimensional Cardiac Late Gadolinium Enhancement MRI at 3.0 Telsa", Journal of Radiological Technology, Japanese Society of Radiological Technology, Dec. 2008, pp. 1554-1561, vol. 64, No. 12.
Hiroshi Watabe, "Image Registration and Fusion for Multimodal Medical Imaging", Japanese Journal of Radiological Technology, Japanese Society of Radiological Technology, Jan. 2003, 1 page, vol. 59, No. 1.
Yoshinobu Sato, et al., "Three-dimensional multi-scale line filter for segmentation and visualization of curvilinear structures in medical images", Medical Image Analysis, Jun. 1998, pp. 143-168, vol. 2, No. 2.
Office Action dated Feb. 22, 2012, issued in corresponding European Patent Application 11186449.2.
Office Action dated Jun. 13, 2013 issued in corresponding European Patent Application No. 11186449.2, 3 pages.
European Communication dated Nov. 8, 2013, issued in European Patent Application No. 11186449.2.

* cited by examiner

*Primary Examiner* — James Kish
(74) *Attorney, Agent, or Firm* — Sughrue Mion, PLLC

(57) ABSTRACT

Using a three-dimensional medical image representing a heart as input, a cardiac function analysis unit calculates a cardiac function evaluation value representing a cardiac function with respect to each of predetermined portions of the heart, using a three-dimensional medical image representing the heart as input, a myocardial infarction analysis unit calculates a myocardial infarction rate representing a degree of myocardial infarction with respect to each of predetermined portions of the heart, and a superimposed image output unit outputs a superimposed image representing the cardiac function evaluation value and the myocardial infarction rate in a superimposing manner such that they are distinguishable from each other in a coordinate system capable of representing each position of the heart in the three-dimensional medical image.

8 Claims, 10 Drawing Sheets

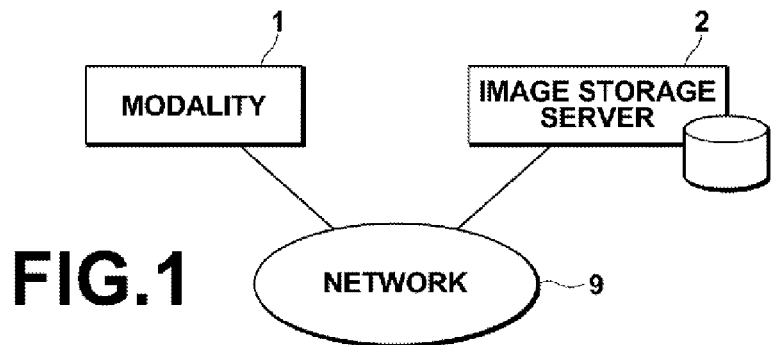
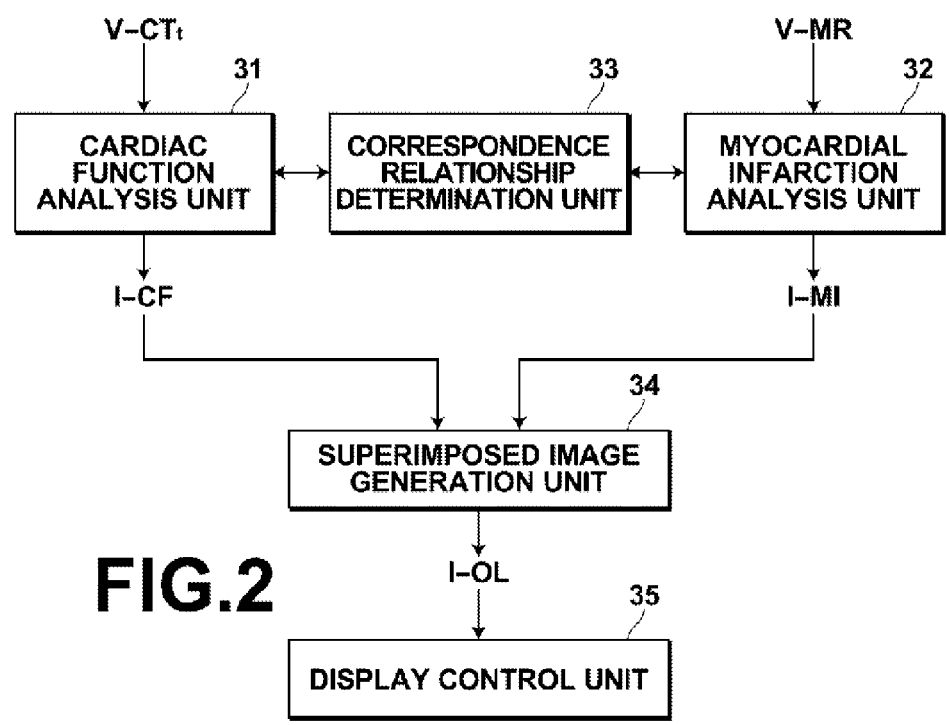

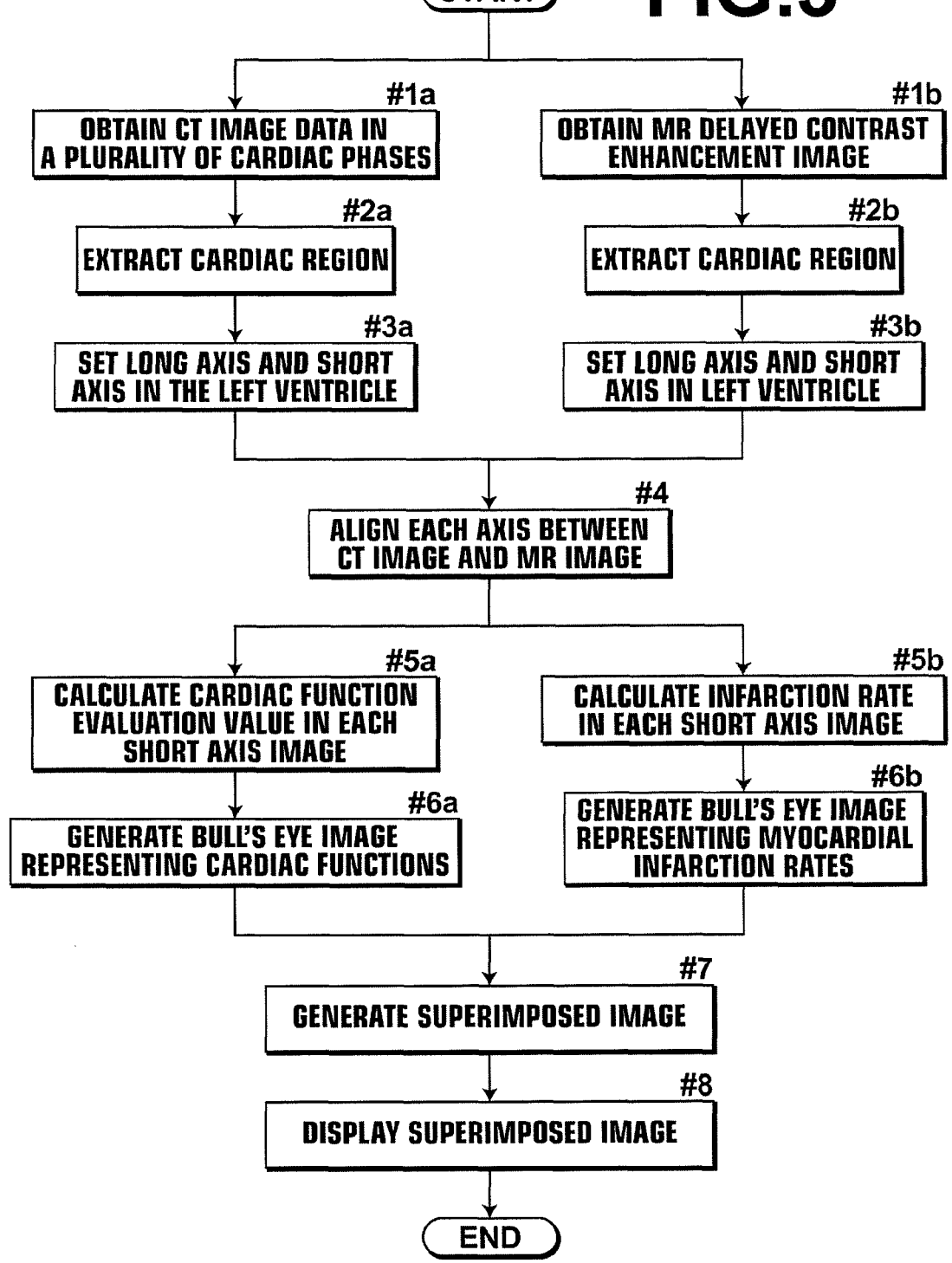

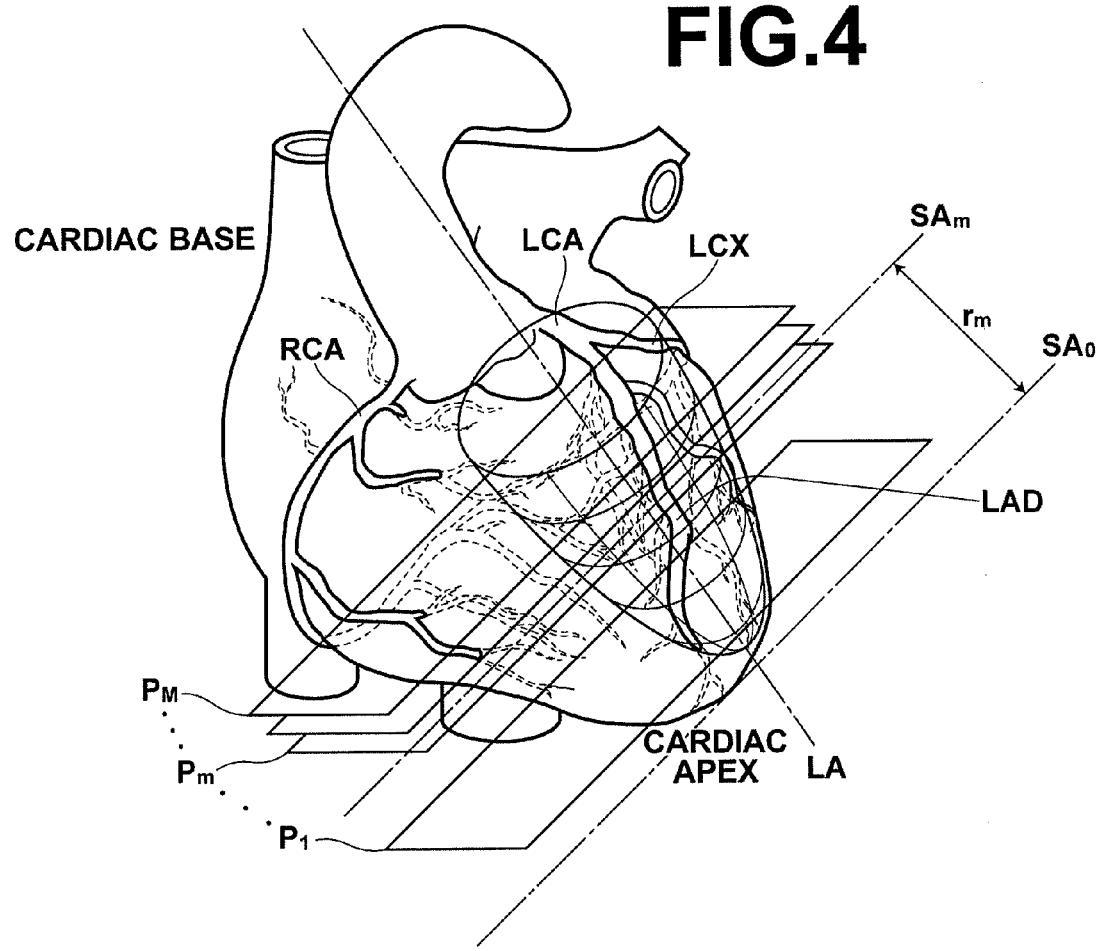

MEDICAL IMAGE DIAGNOSIS ASSISTING
APPARATUS, METHOD, AND PROGRAM

BACKGROUND OF THE INVENTION

1. Field of the Invention

The present invention relates to a medical image diagnosis assisting technology for outputting an image useful for image diagnosis of a cardiac region based on a three-dimensional medical image.

2. Description of the Related Art

Medical image analysis techniques have been advancing rapidly with a wide spread use of multi-detector row computed tomography in clinical practice. For example, in the field of cardiac medicine, it has become possible to obtain a plurality of three-dimensional images within one heartbeat. Along with this, various image diagnosis assisting methods using a three-dimensional medical image of cardiac region have been proposed.

In most cardiac diseases, the supply of blood flow to the myocardium is stopped and the myocardium becomes unable to work, thereby causing cardiac arrest. Therefore, it is necessary to discover a myocardial abnormality by image diagnosis and determine the treatment policy as soon as possible. The angina pectoris and myocardial infarction are the typical examples of cardiac disease caused by ischemia in which the blood flow to the myocardium is reduced. The difference between the angina pectoris and myocardial infarction lies whether or not the myocardium can be recovered in the days ahead. Whereas in the case of angina pectoris, the myocardium can be recovered, it cannot be recovered in the case of myocardial infarction because the myocardium has already been necrotized. In the case of angina pectoris, revascularization therapies, such as the surgery for expanding the constricted portion of the coronary artery causing insufficient blood flow to the myocardium (percutaneous coronary intervention (PCI)) or coronary artery bypassing surgery, may be implemented as the treatment method. Consequently, it is extremely important to diagnose whether the patient has angina pectoris or myocardial infarction.

As image diagnosis for such cardiac diseases, the analysis of cardiac function of left ventricle is performed using a CT or a MR image, whereby a region having abnormal cardiac motion may be detected. The present applicant proposes, for example, a method for fusion displaying a functional image representing cardiac function and an anatomical image representing a coronary artery in a predetermined format in U.S. Patent Application Publication No. 20100074487. In the mean time, MR delayed contrast enhancement analysis for detecting an ischemia area (necrosis area) of myocardium has been drawing attention, and this may indicate which part of the myocardium has an infarction as described, for example, in a non-patent document "Studies of Three-dimensional Cardiac Late Gadolinium Enhancement MRI at 3.0 Tesla", by Ishimoto Takeshi, et al, Journal of Radiological Technology, Japanese Society of Radiological Technology, Vol. 64, No. 12, pp. 1554-1561, Dec. 2008.

SUMMARY OF THE INVENTION

Here, examinations for each analysis described above are performed separately and a result of each analysis is confirmed individually by a doctor, whereby an overall judgment is made. That is, when making an overall judgment based on a cardiac function evaluation result from the cardiac function analysis and a judgment result of infarction portion from the MR delayed contrast enhancement analysis, the doctor imagines the correspondence relationship between the analyses in his/her head and determines the positional relationship.

The present invention has been developed in view of the circumstances described above, and it is an object of the present invention to provide a medical image diagnosis assisting apparatus, method, and program capable of clearly indicating whether or not a myocardial infarction is developed in a portion where cardiac function is deteriorated at the time of image diagnosis of a cardiac region.

A medical image diagnosis assisting apparatus of the present invention is an apparatus, including:

a cardiac function analysis unit configured to calculate, with a three-dimensional medical image representing a heart as input, a cardiac function evaluation value representing a cardiac function with respect to each of predetermined portions of the heart;

a myocardial infarction analysis unit configured to calculate, with a three-dimensional medical image representing the heart as input, a myocardial infarction rate representing a degree of myocardial infarction with respect to each of predetermined portions of the heart; and a superimposed image output unit configured to output a superimposed image representing the cardiac function evaluation value and the myocardial infarction rate in a superimposing manner such that they are distinguishable from each other in a coordinate system (coordinate system of superimposed image) capable of representing each position of the heart in the three-dimensional medical image.

A medical image diagnosis assisting method of the present invention is a computer-implemented method, including the steps of:

calculating, with a three-dimensional medical image representing a heart as input, a cardiac function evaluation value representing a cardiac function with respect to each of predetermined portions of the heart;

calculating, with a three-dimensional medical image representing the heart as input, a myocardial infarction rate representing a degree of myocardial infarction with respect to each of predetermined portions of the heart; and outputting a superimposed image representing the cardiac function evaluation value and the myocardial infarction rate in a superimposing manner such that they are distinguishable from each other in a coordinate system capable of representing each position of the heart in the three-dimensional medical image.

A medical image diagnosis assisting program of the present invention is a program for causing a computer to function as each unit of the medical image diagnosis assisting apparatus described above.

Here, the same three-dimensional medical image or different three-dimensional medical images may be used as input for calculating the cardiac function evaluation value and myocardial infarction rate. A specific example may be three-dimensional medical images representing a heart in one or more of predetermined cardiac phases for the calculation of cardiac function evaluation value. The term "cardiac phase" as used herein refers to a phase in one heartbeat period, including systole and diastole. In the mean time, a three-dimensional medical image representing a delayed enhancement phase of a heart obtained by imaging a subject with an MRI system after predetermined time from the time of administration of a predetermined contrast agent to the subject may be used as input for the calculation of myocardial infarction rate.

In the case where different three-dimensional medical images are used for calculating the cardiac function evaluation value and myocardial infarction rate, it is preferable that a correspondence relationship of anatomical positions of the hearts in the respective three-dimensional medical images is determined, as required. In this case, it is preferable that the superimposed image is an image in which the cardiac function evaluation value and the myocardial infarction rate at corresponding anatomical positions are represented at the same position in the coordinate system based on the correspondence relationship of the anatomical positions. Here, the alignment based on the correspondence relationship of anatomical positions may be performed before the calculation of cardiac function evaluation value and myocardial infarction rate, at the same timing, or after the calculation (at the time of generating the superimposed image).

A specific example of cardiac function evaluation value may be an evaluation value for myocardial wall motion.

As for the myocardial infarction rate, for example, a ratio of a thickness of myocardium where infarction is developed to a thickness of the entire myocardium in each portion as the myocardial infarction rate.

The superimposed image may be an image in which cardiac function evaluation values and myocardial infarction rates of at least some of the respective portions of the heart are represented. For example, only a portion having a cardiac function evaluation value as low as to meet a predetermined criterion (low cardiac function portion) may be represented. As for the myocardial infarction rate, only a portion having a myocardial infarction rate as high as to meet a predetermined criterion (serious myocardial infarction portion) may be represented.

The superimposed image may be an image representing the cardiac function evaluation value and myocardial infarction rate in a coordinate system defined by at least a first coordinate component representing a position in a direction of a long axis connecting a cardiac apex and a cardiac base of the heart and a second coordinate component representing a direction of a radial visual line with a point representing the long axis as the viewpoint in a cross-section perpendicular to the long axis at each point on the long axis. Otherwise, the superimposed image may be an image representing the cardiac function evaluation value and the myocardial infarction rate in a superimposing manner in each portion of the heart viewed from a given direction.

The output mode of the superimposed image may be any mode in which the cardiac function evaluation value and myocardial infarction rate can be represented in a superimposed manner. For example, the output mode can be a mode in which one superimposed image is generated and image data of the image are written into a storage device, a mode in which one superimposed image is generated and outputted as a hard copy, a mode in which two images respectively representing the cardiac function evaluation value and myocardial infarction rate are display-controlled so as to be displayed on a display unit in a superimposed state, or the like.

In the present invention, an arrangement may be adopted in which a coronary artery region is extracted from the three-dimensional medical image and the extracted coronary artery region is further represented in a superimposed manner in the coordinate system.

According to the present invention, a superimposed image representing the cardiac function evaluation value and myocardial infarction rate in a superimposing manner such that they are distinguishable from each other in a coordinate system capable of representing each position of the heart in the three-dimensional medical image may be outputted. This allows calculation results of the cardiac function evaluation value and myocardial infarction rate to be integrally visualized, thereby clearly indicating whether or not a myocardial infarction is developed in a portion where cardiac function is deteriorated. Consequently, distinction between angina pectoris and myocardial infarction may be made more easily and accurately at the time of image diagnosis.

BRIEF DESCRIPTION OF THE DRAWINGS

FIG. 1 is a schematic configuration diagram of a medical image diagnosis system that employs a medical image diagnosis assisting apparatus according to an embodiment of the present invention.

FIG. 2 is a block diagram schematically illustrating a configuration and a processing flow for realizing a medical image diagnosis assisting function (cardiac analysis function) of an embodiment of the present invention.

FIG. 3 is a flowchart illustrating a cardiac analysis processing flow using a medical image diagnosis system of an embodiment of the present invention.

FIG. 4 schematically illustrates a long axis, a short-axis, and cross-sections set in a cardiac region.

DESCRIPTION OF THE PREFERRED EMBODIMENTS

Figure 5:
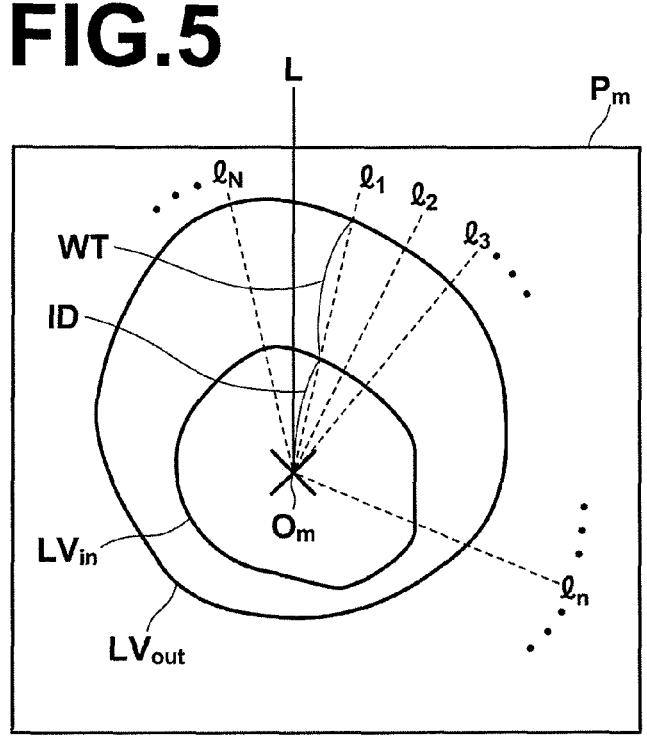
FIG. 5 illustrates calculation processing of a cardiac function evaluation value in a short-axis cross-section.

Hereinafter, a medical image diagnosis system that employs a medical image diagnosis assisting apparatus of an embodiment of the present invention will be described, taking cardiac analysis processing, as an example, in which cardiac function analysis results based on three-dimensional medical images in a plurality of different cardiac phases obtained by multi-detector-row computed tomography and analysis results of infarction areas of myocardium based on a three-dimensional medical image obtained by MR delayed contrast enhancement are displayed in a superimposing manner.

FIG. 1 is a hardware configuration diagram of the medical image diagnosis system, illustrating an overview thereof. As illustrated in FIG. 1, the system includes modality 1, image storage server 2, and image processing workstation 3 communicatively linked to each other via network 9.

Modality 1 is an apparatus for imaging a chest region (cardiac region) of a subject to generate image data of a three-dimensional medical image representing the region and outputting the image data by adding auxiliary information defined by DICOM (Digital Imaging and Communications in Medicine) standard as image information. In the present embodiment, modality 1 includes multi-detector-row computed tomography and MRI.

Image storage server 2 is a computer for storing medical image data obtained by modality 1 and image data of a medical image generated through image processing in image processing workstation 3 in an image database, and managing the image data. Image storage server 2 includes a large capacity external storage device and database management software (e.g., ORDB (Object Relational Database) management software).

Image processing workstation 3 functions as the medical image diagnosis assisting apparatus of the present invention. Image processing workstation 3 performs image processing (including image analysis) on medical image data obtained from modality 1 or image storage server 2 in response to a request from a radiologist and displays a resultant image. It has a known hardware configuration, including a CPU, main memory, auxiliary memory, I/O interface, communication interface, input device (mouse, keyboard, and the like), display monitor, data bus, and the like, with a known operating system installed thereon. The medical image diagnosis assisting processing (cardiac analysis processing) is realized by executing a program (cardiac analysis application) installed from a recording medium, such as a CD-ROM or the like. It may be a program downloaded from a storage device of a server linked via a network, such as the Internet, and installed on the workstation.

The image data storage format and communication between each component via network 9 are based on the DICOM protocol or the like.

FIG. 2 is a block diagram of a part of image processing workstation 3 related to cardiac analysis processing of a first embodiment of the present invention. As illustrated in FIG. 2, the cardiac analysis processing of the present embodiment is realized by cardiac function analysis unit 31, myocardial infarction analysis unit 32, correspondence relationship determination unit 33, superimposed image generation unit 34, and display control unit 35. Image data V-CT$_t$ of CT images in a plurality of cardiac phases "t" (t=1, 2, - - - , T), image data V-MR of a MR delayed contrast enhancement image, image data I-CF of a bull's eye image representing cardiac functions, image data I-MI of a bull's eye image representing infarction rates, and image data I-OL of a superimposed image are data written into and read out from a predetermined memory area of image processing workstation 3 by each processing unit described above.

Next, a flow of the cardiac analysis processing of an embodiment of the present invention will be described based on the flowchart of FIG. 3.

First, when a cardiac analysis target image is selected from an examination list or a series list displayed on a display device of image processing workstation 3 by a user (e.g., image diagnostician), image processing workstation 3 obtains selected CT image data V-CT$_t$ and MR image data V-MR (#1$a$, #1$b$). Then, when an operation for activating a cardiac analysis application is performed by the user, image analysis is initiated for the selected CT image data V-CT$_t$ and MR image data V-MR.

Cardiac function analysis unit 31 extracts a cardiac region, left ventricular cavity region, and myocardial region from each of a plurality of CT image data V-CT$_t$ representing the heart in cardiac phase "t" required for calculating a cardiac function evaluation value CF, to be described later (#2$a$). Then, as schematically illustrated in FIG. 4, cardiac function analysis unit 31 sets a long axis LA-CT$_t$ connecting a cardiac apex and a cardiac base, and M short axes SA-CT$_{t,m}$ (m=1, 2, - - - , M) perpendicular to the long axis LA-CT$_t$ in the extracted cardiac region with respect to each cardiac phase "t" (#3$a$).

In the mean time, myocardial infarction analysis unit 32 extracts a cardiac region, left ventricular cavity region, and myocardial region using the MR image data V-MR as input (#2$b$), and sets a long axis LA-MR and short axes SA-MR$_m$ in the same manner as described above (#3$b$).

Then, correspondence relationship determination unit 33 determines the correspondence relationship of anatomical positions of the hearts represented by the CT image V-CT$_t$ and MR image V-MR and the two images are aligned (#4).

Then, with respect to each of short axis images (FIG. 5) of a plurality of short axis cross-sections P-CT$_{t,1}$ to P-CT$_{t,M}$ (FIG. 4) that passes along the short axes SA-CT$_{t,m}$ (m=1, 2, - - -, M) and perpendicular to the long axis LA-CT$_t$ set in step #3$a$, cardiac function analysis unit 31 calculates a cardiac function evaluation value CF for each direction of radial visual lines l$_1$ to l$_N$ with a point O-CT$_{t,m}$ representing the long axis LA-CT$_t$ in the short axis cross-section P-CT$_{t,m}$ as the viewpoint (#5$a$), and generates a bull's eye image I-CF (FIG. 6) representing cardiac functions (#6$a$).

With respect to each of short axis images (FIG. 7) of a plurality of short axis cross-sections P-MR$_m$ (FIG. 4) that passes along the short axes SA-MR$_m$ (m=1, 2, - - - , M) and perpendicular to the long axis LA-MR set in step #3$b$, myocardial infarction analysis unit 32 calculates an infarction rate MI for each direction of radial visual lines l$_1$ to l$_N$ with a point O$_m$ representing the long axis LA-MR in the short axis cross-section P-MR$_m$ as the viewpoint (#5$b$), and generates a bull's eye image I-MI (FIG. 8) representing infarction rates (#6$b$).

Then, superimposed image generation unit 34 generates a superimposed image I-OL (FIG. 9) in which the bull's eye image I-CF representing cardiac functions and the bull's eye image I-MI representing infarction rates are superimposed (#7), and display control unit 35 causes the generated superimposed image I-OL to be displayed on the display of image processing workstation 3 (#8).

Hereinafter, each processing unit in the present embodiment will be described in detail.

The CT image data V-CT$_t$, the cardiac function analysis target, are obtained by multi-detector-row computed tomography and represent a cardiac region in a plurality of cardiac phases "t". Here, the cardiac phase "t" may be a time interval between R wave to the next R wave in an electrocardiogram normalized as a percentage. In the present embodiment, the cardiac phase is generalized and represented by T phases, t=1, 2, - - - , and T.

The MR image data V-MR, which are the myocardial infarction analysis target, are image data of a T1-weighted image representing delayed enhancement phase obtained with an MRI system by an inversion recovery method or the like after a predetermined time (15 to 20 minutes) from the time of intravenous administration of gadolinium (Gd) contrast agent. The gadolinium (Gd) contrast agent is not taken by normal myocardial cells and distributed in blood and extracellular fluid. In an infarction area in which the myocardium is necrotized, normal myocardial cells are reduced and extracellular fluid is increased due to abnormality of myocardial cells. Consequently, the area becomes a high signal area in the delayed enhancement phase.

As for the method of extracting a cardiac region, left ventricular cavity region, and myocardial region performed by cardiac function analysis unit 31 and myocardial infarction analysis unit 32, any known method may be used. For example, a characteristic amount representing likelihood of a cardiac contour and a characteristic amount representing likelihood of a left ventricle contour may be calculated with respect to each voxel data value constituting a CT image $V\text{-}CT_t$ in each cardiac phase, and a determination may be made as to whether or not each voxel data represents a cardiac contour (epicardium on the outer layer of heart tissue) or a left ventricle contour (endocardium at the boundary between left ventricular cavity and myocardium) by evaluating each of the calculated characteristic amounts based on an evaluation function obtained in advance through machine learning. By repeating the determination, voxel data representing contours of the entire heart and left ventricle are determined, whereby the area within the cardiac contour, area within the left ventricle contour, and area between the two contours are extracted as the cardiac region, left ventricular cavity region, and myocardial region respectively. The evaluation function may be obtained using, for example, AdaBoost algorithm as described, for example, in Japanese Unexamined Patent Publication No. 2007-307358. Further, other machine learning methods and statistical modeling methods, such as linear discriminant method, neural network, support vector machine, and the like, may also be used for the extraction of each region. Further, a user interface may be provided to allow the user to manually correct the extraction result of heart, ventricular cavity, and myocardium. The manual correction may be performed, for example, by displaying the extraction result of each region in a short axis image or a long axis image of a cross-section along the long axis and accepting an operation for changing the boundary of a region desired to be changed.

Cardiac function analysis unit 31 may set a long axis $LA\text{-}CT_t$ and short axes $SA\text{-}CT_{t,m}$ (m=1, 2, - - - , M) in the following manner. That is, with respect to the extracted left ventricle region, a long axis $LA\text{-}CT_t$ connecting the cardiac apex and cardiac base through an approximate center of the left ventricle is set, and M short axes $SA\text{-}CT_{t,m}$ (m=1, 2, - - - , M) perpendicular to the long axis $LA\text{-}CT_t$ are set at each point on the long axis $LA\text{-}CT_t$, as schematically illustrated in FIG. 4. Here, the long axis $LA\text{-}CT_t$ may be set automatically by calculating coordinates of positions of the cardiac apex and the center of the left ventricle from the extraction result of cardiac region. Each position of the short axis $SA\text{-}CT_{t,m}$ on the long axis $LA\text{-}CT_t$ is set by default or based on a parameter set by the user, such as the number of short axis images (the value of M), distance between short axis cross-sections, or the like. Myocardial infarction analysis unit 32 may set a long axis $LA\text{-}MR$ and short axes $SA\text{-}MR_m$ (m=1, 2, - - - , and M) in the same manner as described above. Further, a user interface may be provided to allow the user to manually correct the position or direction of the automatically set long axis $LA\text{-}CT_t$ or $LA\text{-}MR$. For example, the automatically set long axis $LA\text{-}CT_t$ or $LA\text{-}MR$ may be displayed on the screen with the cardiac region image to allow the long axis $LA\text{-}CT_t$ or $LA\text{-}MR$ to be moved or rotated by a drag operation.

Correspondence relationship determination unit 33 may align the CT image $V\text{-}CT_t$ with MR image $V\text{-}MR$ by obtaining an image transformation function that maximizes mutual information between the MR image $V\text{-}MR$ and a CT image $V\text{-}CT_{T0}$ in a cardiac phase T0 which is the same or close to the cardiac phase of the MR image $V\text{-}MR$ and performing a rigid or non-rigid transformation of the MR image $V\text{-}MR$ by the image transformation function. More specifically, CT short axis images of a plurality of short axis cross-sections $P\text{-}CT_{T0}$, 1 to $P\text{-}CT_{T0}$, M, each passing along each short axis $SA\text{-}CT_{T0,m}$ and perpendicular to a long axis $LA\text{-}CT_{T0}$, from CT image data $V\text{-}CT_{T0}$. In the mean time, MR short axis images of a plurality of short axis cross-sections $P\text{-}MR_1$ to $P\text{-}MR_M$, each passing along each short axis $SA\text{-}MR$, and perpendicular to the long axis $LA\text{-}MR$, from the MR image data $V\text{-}MR$. Then, alignment is performed with respect to each pair of CT short axis image and MR short axis image at short axis positions corresponding to each other using mutual information. Alternatively, the alignment may be performed manually through mouse operation by the user with respect to each pair described above. (For more information, reference is made, for example, to a literature "Image Registration and Fusion for Multimodal Medical Imaging" by H. Watabe, Japanese Journal of Radiological Technology, Japanese Society of Radiological Technology, Vol. 59, No. 1, pp. 60-65, January 2003, and the like.)

As illustrated in FIG. 5, a cardiac function evaluation value CF is calculated in each CT short axis cross-section $P\text{-}CT_{t,m}$ with respect to each of a plurality of line segments $l_n$ (n= 1, 2, - - - , and N) radially extending along the short axis cross-section $P\text{-}CT_{t,m}$ from the intersection point $O\text{-}CT_{t,m}$ between the long axis $LA\text{-}CT_t$ and short axis cross-section $P\text{-}CT_{t,m}$ or with respect to each section divided by each ling segment $l_n$. Specific examples of cardiac function evaluation values CF and calculation methods thereof will be described hereinafter.

Specific examples of cardiac function evaluation value CF that can be calculated from CT image data $V\text{-}CT_t$ of a single cardiac phase are ventricular internal diameter and wall thickness. The ventricular internal diameter is a distance from the intersection point $O\text{-}CT_{t,m}$ to the boundary $LV_{in}$ between the ventricular cavity and myocardium along each line segment $l_n$ (e.g., distance ID on the line segment $l_1$ in FIG. 5) in each CT short axis image. The wall thickness is a difference between the distance from the intersection point $O\text{-}CT_{t,m}$ to the boundary $LV_{out}$ of the heart along the line segment $l_n$ and the distance from the intersection point $O\text{-}CT_{t,m}$ to the boundary $LV_{in}$ between the ventricular cavity and myocardium along the line segment $l_n$ (e.g., distance WT on the line segment $l_1$ in FIG. 5) in each CT short axis image. In the case where these cardiac evaluation values CF are calculated for each cardiac phase "t" and a bull's eye image is generated with respect to each cardiac phase, these cardiac evaluation values CF may be displayed as a motion picture. Otherwise, they may be calculated only for particular cardiac phases which are important for image diagnosis, such as end-diastole and end-systole. In this case, the alignment between the CT image $V\text{-}CT_t$ and MR image $V\text{-}MR$ described above may be performed between the CT image $V\text{-}CT_t$ and MR image $V\text{-}MR$ in the particular cardiac phase regardless of the correspondence in cardiac phase between the two images.

Specific examples of cardiac function evaluation value CF that can be calculated from CT image data $V\text{-}CT_t$ in a plurality of cardiac phases are local ejection fraction, wall thickness variance, and wall motion. The term "local ejection fraction" as used herein refers to the ejection fraction of each divided section in the left ventricle. The term "ejection fraction" as used herein refers to the ratio of the difference in volume (ejection volume) between the end-diastole and end-systole to the volume at end-diastole. In the present embodiment, the local ejection fraction may be obtained by the formula given below with respect to each section divided by each line segment $l_n$ in each short axis image.

(Area (Volume) at End-Diastole−Area (Volume) at End-Systole)×100/Area at End-Diastole The term "wall thickness variance" as used herein refers to the difference in myocardial thickness (wall thickness) between the end-systole and end-diastole. The term "wall thickening" as used herein refers to the ratio of the difference in myocardial thickness (wall thickness) between end-systole and end-diastole to the myocardial thickness (wall thickness) at end-systole. The term "wall motion" as used herein refers to the difference in ventricular diameter between end-diastole and end-systole.

In the case where a cardiac function evaluation value is calculated from CT image data V-CT$_t$ in a plurality of cardiac phases, it is preferable that the alignment of CT image data V-CT$_t$ between cardiac phases used for the calculation is performed before the cardiac function evaluation value CF is calculated. For example, the alignment between a CT image V-CT$_{T1}$ in phase T1 and a CT image V-CT$_{T2}$ in phase T2 may be performed by obtaining an image transformation function that maximizes the correlation coefficient between the images and performing a rigid or non-rigid transformation on either one of the CT images. More specifically, alignment using the correlation coefficient is performed with respect to each pair of CT short axis images at short axis positions corresponding to each other, as in the alignment between the CT image V-CT$_t$ and MR image V-MR. Alternatively, alignment in may be performed manually through mouse operation by the user with respect to each pair.

Figure 7:
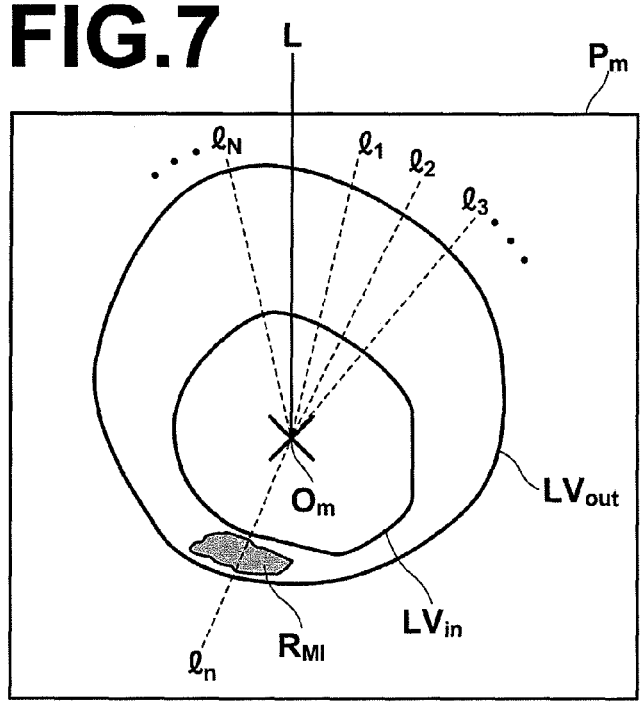
FIG. 7 illustrates calculation processing of infarction rate in a short-axis cross-section.

In the mean time, the infarction rate MI is the ratio of an infarction area to the entire myocardial region in the a short axis cross-section P-MR$_m$ with respect to, for example, each of a plurality of line segments $l_n$ (n=1, 2, - - -, and N) radially extending along the MR short axis cross-section P-MR$_m$ from the intersection point O-MR$_m$ between the long axis LA-MR and short axis cross-section P-MR$_m$ as illustrated in FIG. 7, and may be obtained by the formula given below with respect to each ling segment $l_n$.

Thickness of Infarction area R$_{MI}$×100/Thickness of Entire Myocardial Region (Wall Thickness: Distance between LV$_{in}$ and LV$_{out}$) Alternatively, the infarction rate MI may be obtained with respect to each segment divided by each line segment $l_n$ by the formula given below.

Area of Myocardial Infarction area R$_{MI}$×100/Area of Entire Myocardial Region
As described above, a myocardial infarction area R$_{MI}$ has a higher signal value than that of a normal myocardial region, and use of a threshold value that can make distinction between infarction area and normal region allows a voxel data having a higher signal value than the threshold value to be extracted as an infarction area R$_{MI}$.

Figure 6:
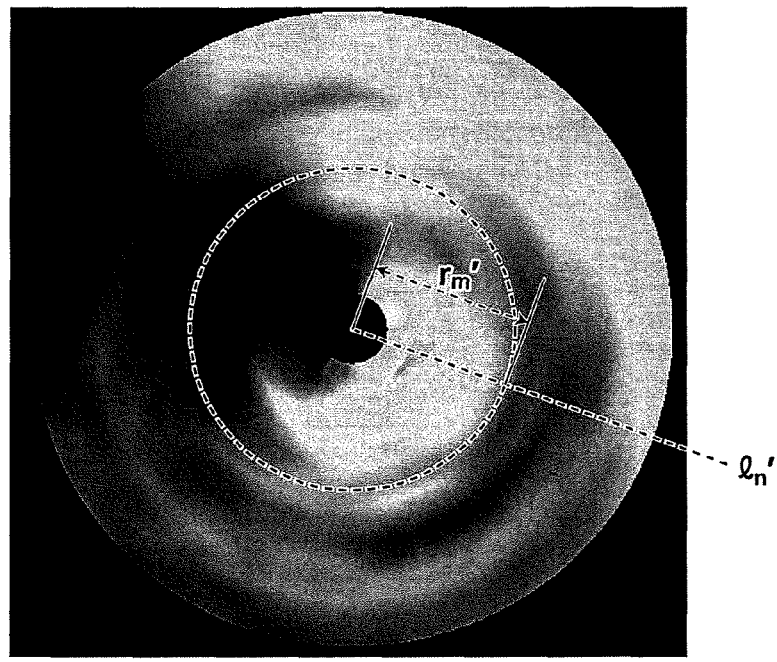
FIG. 6 shows an example bull's eye image representing cardiac functions.

The bull's eye image I-CF representing cardiac function evaluation values CF may be generated by disposing cardiac function evaluation values obtained from each of CT short axis cross-section P-CT$_{t,1}$ to P-CT$_{t,M}$ on circumferences of concentric circles having different radii according to the distance of each cross-section from the cardiac apex. More specifically, the evaluation values are disposed such that the closer the cross-section to the cardiac apex the smaller the radius of the circumference. Alternatively, the evaluation values may be disposed such that the closer the cross-section to the cardiac base, the smaller the radius of the circumference. FIG. 6 shows an example bull's eye image I-CF representing cardiac function evaluation values CF. As shown in FIG. 6, the distribution of cardiac function evaluation values CF in CT short axis cross-section P-CT$_{t,m}$ (FIG. 4) at a distance $r_m$ from the cardiac apex is disposed on a circumference with a radius $r_m'$ corresponding to the distance $r_m$ from the cardiac apex in the bull's eye image I-CF. Further, the distribution of cardiac function evaluation values CF in each CT short axis cross-section P-CT$_{t,m}$ is represented such that the direction of each line segment $l_n$ (FIG. 5) in the CT short axis cross-section P-CT$_{t,m}$ corresponds to the direction of the line segment $l_n'$ in the bull's eye image I-CF. Cardiac function evaluation values CF are displayed, for example, in different colors according to the value. Further, a color may be allocated to a predetermined range of cardiac function evaluation values.

Figure 8:
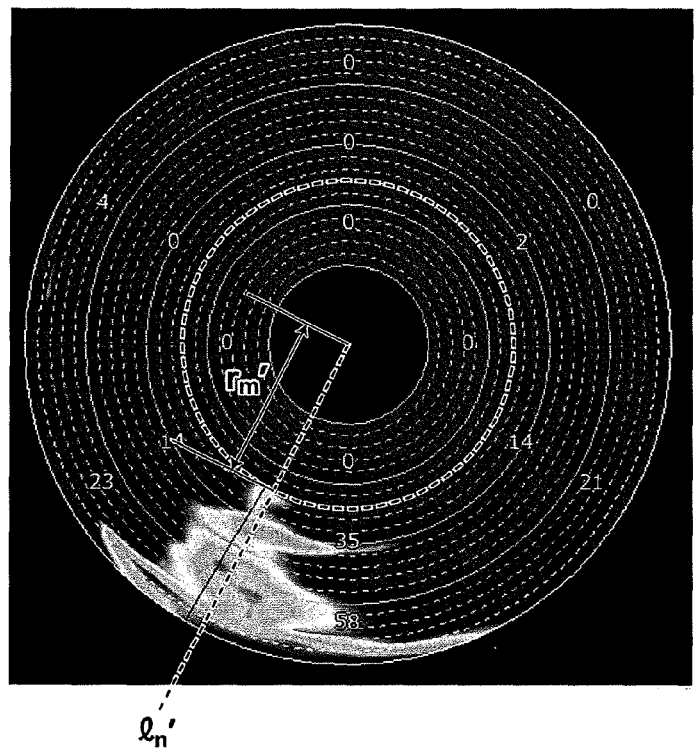
FIG. 8 shows an example bull's eye image representing infarction rates.

The bull's eye image I-MI representing infarction rates MI is generated in the same manner as the bull's eye image representing cardiac function evaluation values CF. FIG. 8 shows an example bull's eye image representing infarction rates MI. As shown in FIG. 8, the distribution of infarction rates MI in a MR short axis cross-section P-MR$_m$ (FIG. 4) at a distance $r_m$ from the cardiac apex is disposed on a circumference with a radius $r_m'$ corresponding to the distance $r_m$ from the cardiac apex in the bull's eye image I-MI. Further, the distribution of infarction rates in each MR short axis cross-section P-MR$_m$ is represented such that the direction of each line segment $l_n$ (FIG. 7) in the MR short axis cross-section P-MR$_m$ corresponds to the direction of the line segment $l_n'$ in the bull's eye image I-MI. In the present embodiment, a specific density value is allocated only to a region having an infarction rate MI greater than or equal to a predetermined value (e.g., 90%), but different gray values may be allocated according to the value of infarction rate MI. Further, an arrangement may be adopted in which the range of values of infarction rate represented in the bull's eye image I-MI is changed by the user.

Figure 9:
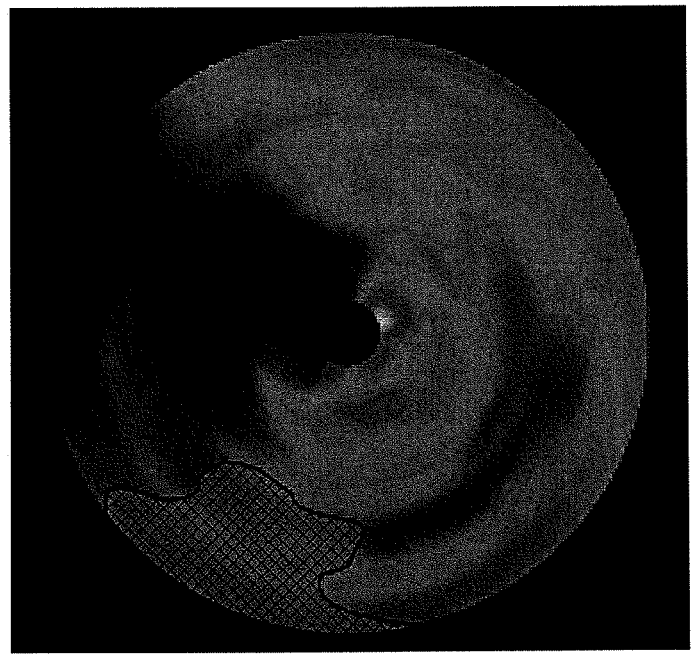
FIG. 9 shows an example bull's eye image in which cardiac function evaluation values and infarction rates are superimposed.

The superimposed image I-OL is generated by superimposing the bull's eye image I-MI representing infarction rates MI on the bull's eye image I-CF representing cardiac function evaluation values CF after making the bull's eye image I-MI translucent. Here, the positional correspondence relationship between the bull's eye images I-CF and I-MI has already been determined and aligned by correspondence relationship determination unit 33. Thus, superimposed image generation unit 34 may simply superimpose each point having corresponding coordinate values in each image. FIG. 9 shows an example superimposed image I-OL generated from the bull's eye image I-CF representing cardiac function evaluation values CF shown in FIG. 6 and the bull's eye image I-MI representing infract rates MI shown in FIG. 8. As shown in FIG. 9, cardiac function evaluation values CF and infarction rates MI are displayed in different display modes (color, density, hatching, and the like) such that both can be visually recognized.

As described above, according to an embodiment of the present invention, superimposed image generation unit 34 outputs a superimposed image I-OL representing cardiac function evaluation values CF calculated by cardiac function analysis unit 31 and infarction rates MI calculated by myocardial infarction analysis unit 32 in a superimposing manner such that they are distinguishable from each other in a coordinate system capable of representing each position of a heart. This may integrally visualize the two calculation results of cardiac function evaluation values and infarction rates, and may clearly indicate to the user as to whether or not an infarction of myocardium is developed in a portion where the cardiac function is deteriorated. Consequently, judgment of angina pectoris or myocardial infarction may be made easily and accurately in image diagnosis.

Further, correspondence relationship determination unit 33 determines the correspondence relationship in cardiac anatomical positions between a CT image V-$CT_t$ used for calculating cardiac function evaluation values and a MR image V-MR used for calculating infarction rates MI and the two images are aligned. This may reduce the error of a position in the superimposed image I-OL generated by superimposed image generation unit 34 where a cardiac function evaluation value CF and an infarction rate MI at the same anatomical position are represented, thereby contributing to the improvement of diagnostic accuracy.

Further, the superimposed image I-OL generated by superimposed image generation unit 34 is an image represented by a coordinate system defined by a first coordinate component indicating the position in the direction of the long axis LA-$CT_t$ or LA-MR connecting the cardiac apex and cardiac base of a heart and a second coordinate component indicating directions of radial visual lines with the point representing the long axis LA-$CT_t$ or LA-MR as the viewpoint in a short axis cross-section P-$CT_{t,m}$ or P-$MR_m$ perpendicular to the long axis LA-$CT_t$ or LA-MR at each position on the long axis LA-$CT_t$ or LA-MR. Thus, cardiac function evaluation values CF and infarction rates MI over the whole circumference of the cardiac (left ventricle) wall are represented in one image and the range that can be viewed at one glance is broadened, thereby contributing to diagnostic efficiency.

Further, with respect to the infarction rate MI, only a portion having a high infarction rate that meets a predetermined criterion is represented in the superimposed image I-OL. This may prevent the superimposed image I-OL from becoming complicated by the superimposition of cardiac function evaluation values and infarction rates MI, and distribution of the respective values from becoming difficult to observe, so that a myocardial portion where infarction is developed, which is important in diagnosis, can be easily understood.

In the embodiment described above, the cardiac function evaluation values CF and infarction rates MI are displayed in a bull's eye format, but the display mode, i.e., coordinate system of the superimposed image I-OL is not limited to this.

Figure 10:
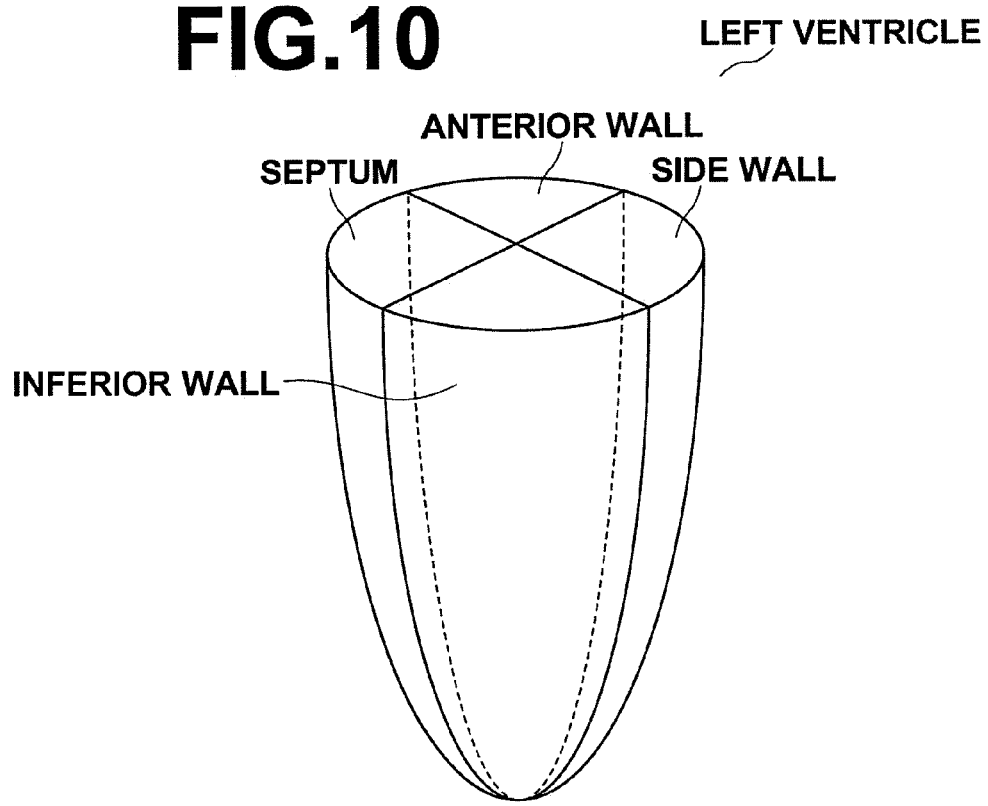
FIG. 10 schematically illustrates four segments of a left ventricle.
Figure 11:
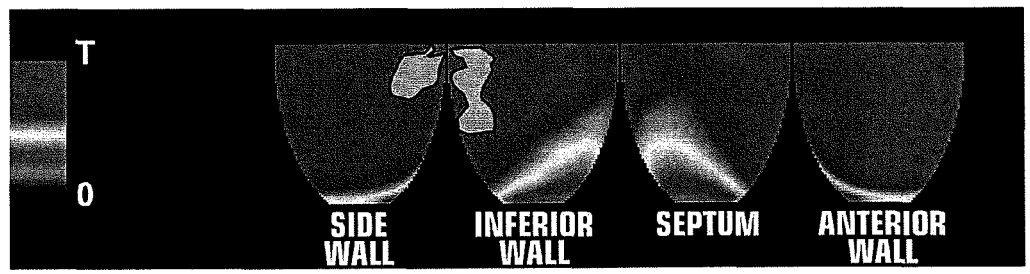
FIG. 11 illustrates an example topographic map image in which a cardiac function evaluation value and an infarction rate are superimposed.

For example, a topography map display shown in FIG. 11 may be used. This is a display mode in which the left ventricle is divided into four segments of side wall, inferior wall, septum, and anterior wall, as schematically illustrated in FIG. 10, and spread out such that the wall of the left ventricle is cut open at the boundary of each segment.

Figure 12:
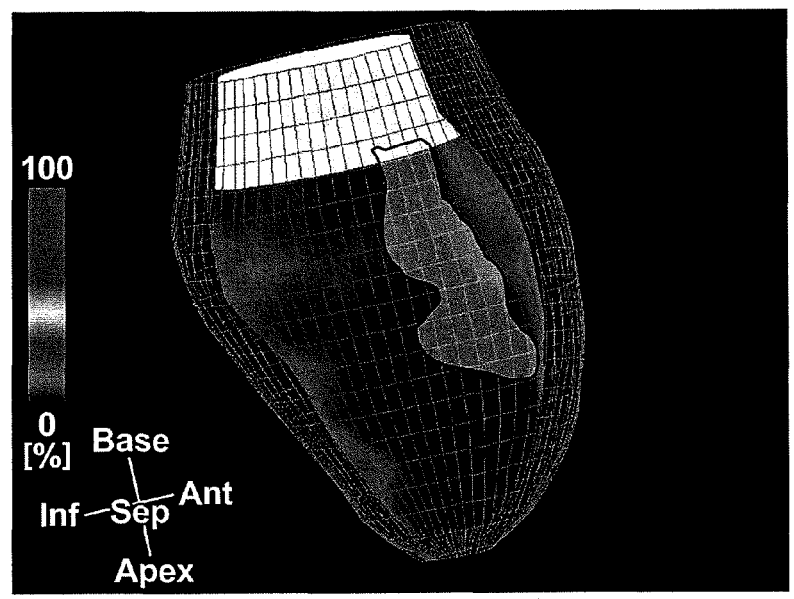
FIG. 12 illustrates an example image in which a cardiac function evaluation values and infarction rates are superimposed.

Further, cardiac function evaluation values CF and infarction rates MI may be mapped and displayed in a pseudo three-dimensional image representing a heart, as shown in FIG. 12. The example shown in FIG. 12 uses the internal wall $VL_{in}$ and external wall $LV_{out}$ of myocardial region of the left ventricle extracted by cardiac function analysis unit 31 in which the external wall $LV_{out}$ of the left ventricle is displayed in mesh mode while the internal wall $LV_{in}$ is displayed by surface rendering, and the cardiac function evaluation values CF and infarction rates MI are mapped on the surface of the internal wall $LV_{in}$ of the left ventricle. The mapping positions of the cardiac function evaluation values CF or infarction rates MI are intersection points between the plurality of line segments $l_n$ (n=1, 2, - - -, and N) shown in FIG. 5 or 7 and the left ventricle internal wall $LV_{in}$. This display mode allows distributions of the cardiac function evaluation values and infarction rates MI to be observed while visualizing the anatomy of the heart or left ventricle to a certain degree, whereby the anatomical position of an abnormal portion of cardiac function or of an infarcted portion is understood easily. On the other hand, this display mode does not allow the user to view the cardiac function evaluation values CF and infarction rates MI over the whole circumference of the left ventricle wall, and it is preferable that the pseudo three-dimensional image is rotatable by changing the position of the viewpoint or visual line direction in response to a user operation using a mouse or the like.

Figure 13:
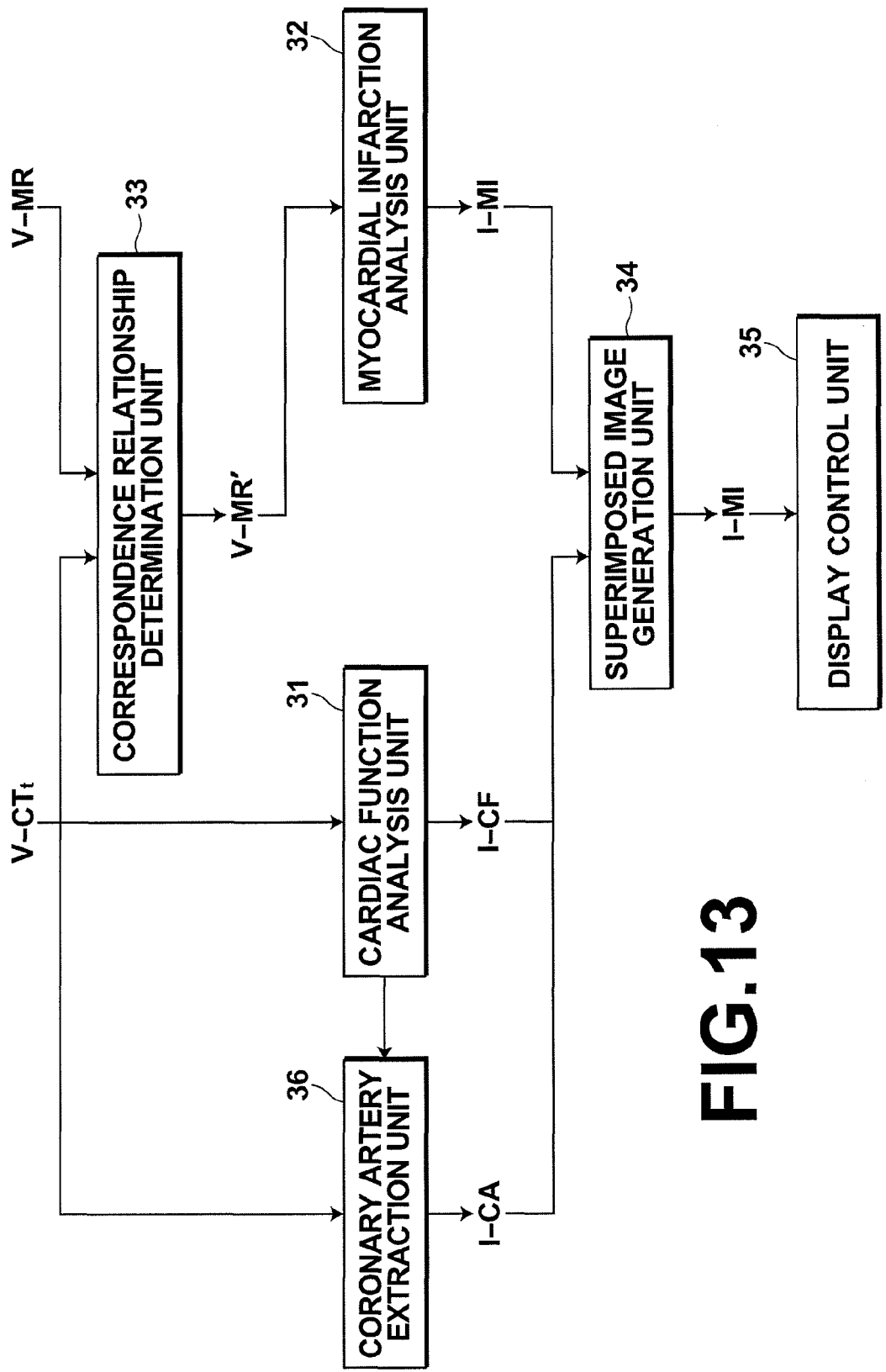
FIG. 13 is a block diagram schematically illustrating a configuration and a processing flow for realizing a medical image diagnosis assisting function (cardiac analysis function) of a modification of an embodiment of the present invention.

In the embodiment described above, only the cardiac function evaluation values CF and infarction rates MI are displayed in a superimposing manner, but an anatomy of the coronary artery may also be displayed in a superimposing manner. FIG. 13 is a block diagram for this modification. As illustrated in FIG. 13, this modification additionally includes coronary artery extraction unit 36 in comparison with the embodiment described above.

Coronary artery extraction unit 36 extracts a coronary artery region I-CA from a CT image V-$CT_t$ by a known method. For example, the coronary artery region I-CA may be extracted by extracting a cardiac region from the image data V-$CT_t$ of a CT image, performing a multi-resolution conversion on an image representing the cardiac region, performing eigenvalue analysis of Hessian matrix on an image of each resolution, integrating analysis results of the image of each resolution to extract the coronary artery I-CA as aggregation of line structures (blood vessels) of various sizes from the cardiac region, which may then be stored in a predetermined memory area as described, for example, in "Three-dimensional multi-scale line filter for segmentation and visualization of curvilinear structures in medical images" by Y. Sato, et al., Medical Image Analysis, June 1998, Vol. 2, No. 2, p.p. 143-168. In the present modification, the extraction of the cardiac region is performed as processing common to that of cardiac function analysis unit 31. Coronary artery extraction unit 36 may further generate tree structure data by connecting the center point of each of the extracted line structures using a minimum spanning tree algorithm, then obtain, at each point on a core line (each node of the tree structure data) connecting center points of the extracted coronary artery, a cross-section perpendicular to the core line, recognize a contour of the coronary artery using a known segmentation method, such as Graph-Cuts method, in each cross-section, and relate information representing the contour to each node of the tree-structure data.

Figure 14:
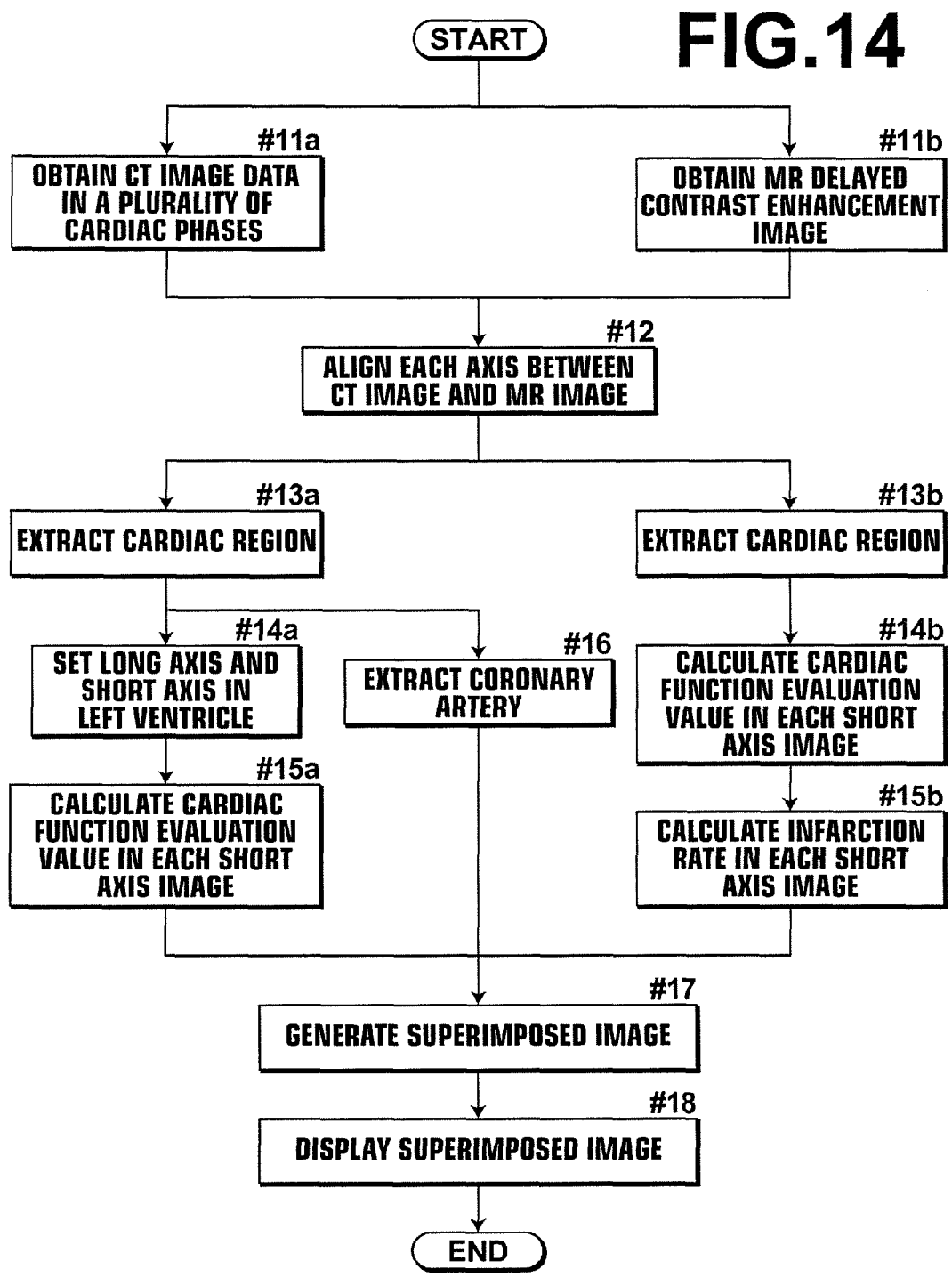
FIG. 14 is a flowchart illustrating a cardiac analysis processing flow using a medical image diagnosis system of a modification of an embodiment of the present invention.
Figure 15:
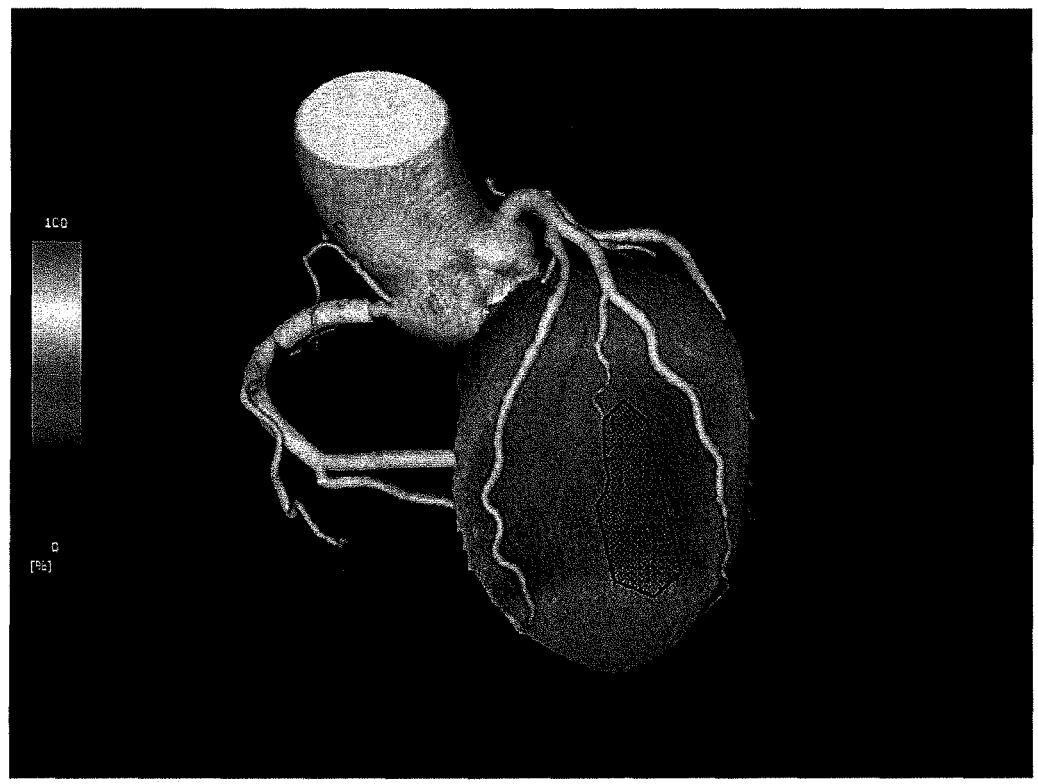
FIG. 15 shows an example volume rendering image in which an anatomy of coronary artery, cardiac function evaluation values, and an infarction rate are superimposed.

FIG. 14 is a flowchart illustrating a processing flow in the present modification. As shown in FIG. 14, image processing workstation 3 obtains CT image data V-$CT_t$ and MR image data V-MR (#11a, #11b), and correspondence relationship determination unit 33 determines the correspondence relationship between the anatomical position of the heart represented by each of the CT image V-$CT_t$ and MR image V-MR and aligns the two images (#12), as in the aforementioned embodiment. Here, it is assumed that the MR image V-MR is transformed and the aligned MR image V-MR' is stored in a predetermined memory area. Then, when a cardiac analysis application is activated by the user, cardiac function analysis unit 31 extracts a cardiac region, left ventricular cavity region, and myocardial region from the CT image data V-$CT_t$ (#13a), sets a long axis LA-CTt and short axes SA-$CT_{t,m}$, and calculates cardiac function evaluation values (#15a), as in the aforementioned embodiment. In the mean time, coronary artery extraction unit 36 extracts a coronary artery region I-CA from the cardiac region extracted in step #13a (#16). Further, myocardial infarction analysis unit 32 extracts a cardiac region, left ventricular cavity region, and myocardial region using the MR image data V-MR as input (#13b), then sets a long axis LA-MR and short axes SA-$MR_m$ (#14b), and calculates infarction rates MI (#15b), as in the aforementioned embodiment. Then, superimposed image generation unit 34 generates a pseudo three-dimensional image I-OL in which the coronary artery region I-CA, cardiac function evaluation values CF, and infarction rates MI are superimposed, as shown in FIG. 15 (#17). The pseudo three-dimensional image I-OL may be generated, for example, by combining voxel data representing the coronary artery I-CA, and voxel data representing the cardiac functions CF and infarction rates MI by alpha blending or volume rendering (for more information, reference is made to U.S. Patent Application Publication No. 20090096787, and the like). Display control unit 35 causes the generated superimposed image to be displayed on the display of image processing workstation 3 (#18) Here, it is preferable that the pseudo three-dimensional image is rotatable by changing the position of the viewpoint or visual line direction in response to a user operation using a mouse or the like.

In the aforementioned explanation, the pseudo three-dimensional image is generated as a superimposed image, but an arrangement may be adopted in which a bull's eye image representing the coronary artery is generated and a superimposed image I-OL is generated in which a bull's eye images, representing the coronary artery region I-CA, cardiac evaluation values CF, and infraction rates MI respectively, are superimposed (for more information, reference is made to U.S. Patent Application Publication No. 20090096787, and the like).

As described above, according to the present modification, a superimposed image I-OL is generated by further superimposing an anatomy of the coronary artery I-CA on an image in which cardiac function evaluation values CF and infarction rates MI are superimposed. This allows a coronary artery that supplies oxygen or the like to a myocardial area having abnormal cardiac function or infarction to be easily understood and collaboration with a known application for analyzing the coronary artery to be easy. Consequently, further improvement in diagnostic efficiency and accuracy may be expected.

It should be appreciated that the embodiment and modification described above are illustrative purposes only and should not be used as limiting the technical scope of the present invention. Further, it should be appreciated that various changes and modifications made in the system configuration, hardware configuration, processing flow, module configuration, user interface, specific processing content, and the like of the embodiment described above without departing from the spirit of the present invention are also included in the technical scope of the present invention.

For example, the order of processing in processing steps shown in parallel in FIGS. 3 and 14 is not limited to the order described above, and they may be performed in reverse or in parallel. For example, the steps #1*a*, #2*a*, #3*a* shown in FIG. 3 may be performed before, after, or simultaneously with the steps #1*b*, #2*b*, #3*b*.

The superimposing display of cardiac function evaluation values CF and infarction rates MI may be realized by causing a bull's eye image I-CF representing the cardiac function and a bull's eye image representing the infraction rate MI to be continuously switched at a predetermined time interval and displayed on the display of image processing workstation 3 by display control unit 35, instead of providing superimposed image generation unit 34.

What is claimed is:

1. A medical image diagnosis assisting apparatus, comprising:
a cardiac function analyzer configured to calculate, with one or more of first three-dimensional medical images representing a heart as input, a cardiac function evaluation value representing a cardiac function with respect to each of predetermined portions of the heart;
a myocardial infarction analyzer configured to calculate, with one or more second three-dimensional medical images representing the heart as input, a myocardial infarction rate representing a degree of myocardial infarction with respect to each of predetermined portions of the heart; and
a superimposed image generator configured to output a superimposed image representing the cardiac function evaluation value and the myocardial infarction rate in a superimposing manner such that they are distinguishable from each other in a coordinate system capable of representing each position of the heart in the three-dimensional medical image;
wherein:
the cardiac function analyzer is further configured to calculate, with the one or more of first three-dimensional medical images representing the heart in one or more of predetermined cardiac phases respectively, a cardiac function evaluation value for myocardial wall motion;
the myocardial infarction analyzer is further configured to calculate a myocardial infarction rate from the one or more second three-dimensional medical images representing a delayed enhancement phase of a heart obtained by imaging a subject with an MRI system after predetermined time from the time of administration of a predetermined contrast agent to the subject; and
wherein:
the apparatus further comprises a correspondence relationship determinator configured to determine a correspondence relationship of anatomical positions of the heart in the first and second three-dimensional medical images;
the superimposed image is an image in which the cardiac function evaluation values and the myocardial infarction rate at corresponding anatomical positions are represented at the same position in the coordinate system based on the correspondence relationship of the anatomical positions;
the medical image diagnosis assisting apparatus is configured to generate and display a topography map; and
the medical image diagnosis assisting apparatus is configured to display an anatomy of the coronary artery with the cardiac function evaluation values and infraction rates in a superimposing manner;
wherein:
the apparatus comprises a coronary artery extractor configured to extract a coronary artery region from a three-dimensional medical image representing the heart; and
wherein the superimposed image output generator outputs a superimposed image further representing the extracted coronary artery region in a superimposing manner in the coordinate system, said coronary artery region being distinguishable in the superimposed image.

2. The apparatus of claim 1, wherein the coordinate system is defined by at least a first coordinate component representing a position in a direction of a long axis connecting a cardiac apex and a cardiac base of the heart and a second coordinate component representing a direction of a radial visual line with a point representing the long axis as the viewpoint in a cross-section perpendicular to the long axis at each point on the long axis.

3. The apparatus of claim 1, wherein the superimposed image output generator outputs a superimposed image representing the cardiac function evaluation value and the myocardial infarction rate in a superimposing manner in each portion of the heart viewed from a given direction.

4. The apparatus of claim 1, wherein the myocardial infarction analyzer further calculates a ratio of a thickness of myocardium where infarction is developed to a thickness of the entire myocardium in each portion as the myocardial infarction rate.

5. The apparatus of claim 1, wherein the superimposed image output generator further outputs a superimposed image representing, with respect to myocardial infarction rates, only a portion having a myocardial infarction rate as high as to meet a predetermined criterion in a superimposing manner in the coordinate system.

6. The apparatus of claim 1, wherein the first three-dimensional medical images are obtained by multi-detector-row computed tomography and the second three-dimensional medical image is obtained by MR delayed contrast enhancement.

7. A computer-implemented medical image diagnosis assisting method, comprising the steps of:
   calculating, with a three-dimensional medical image representing a heart as input, a cardiac function evaluation value representing a cardiac function with respect to each of predetermined portions of the heart;
   calculating, with a three-dimensional medical image representing the heart as input, a myocardial infarction rate representing a degree of myocardial infarction with respect to each of predetermined portions of the heart;
   outputting a superimposed image representing the cardiac function evaluation value and the myocardial infarction rate in a superimposing manner such that they are distinguishable from each other in a coordinate system capable of representing each position of the heart in the three-dimensional medical image;
   generating and displaying a topography map; and
   displaying an anatomy of the coronary artery with the cardiac function evaluation value CF and infraction rates MI in a superimposing manner;
   further comprising:
   extracting a coronary artery region from the three-dimensional medical image representing the heart; and
   wherein the superimposed image further representing the extracted coronary artery region in the coordinate system, said coronary artery region being distinguishable in the superimposed image.

8. A non-transitory computer readable recording medium on which is recorded a medical image diagnosis assisting program for causing a computer to execute the following operations:
   calculating, with a three-dimensional medical image representing a heart as input, a cardiac function evaluation value representing a cardiac function with respect to each of predetermined portions of the heart;
   calculating, with a three-dimensional medical image representing the heart as input, a myocardial infarction rate representing a degree of myocardial infarction with respect to each of predetermined portions of the heart;
   outputting a superimposed image representing the cardiac function evaluation value and the myocardial infarction rate in a superimposing manner such that they are distinguishable from each other in a coordinate system capable of representing each position of the heart in the three-dimensional medical image;
   generating and displaying a topography map; and
   displaying an anatomy of the coronary artery with the cardiac function evaluation value CF and infraction rates MI in a superimposing manner;
   further comprising;
   extracting a coronary artery region the three-dimensional medical image representing the heart; and
   wherein the superimposed image further representing the extracted coronary artery region in the coordinate system, said coronary artery region being distinguishable in the superimposed image.

* * * * *